US007018792B2

(12) United States Patent
Swanson et al.

(10) Patent No.: US 7,018,792 B2
(45) Date of Patent: Mar. 28, 2006

(54) INFLUENZA SENSOR

(75) Inventors: Basil I. Swanson, Los Alamos, NM (US); Xuedong Song, Los Alamos, NM (US); Clifford Unkefer, Los Alamos, NM (US); Louis A. Silks, III, Los Alamos, NM (US); Jurgen G. Schmidt, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 12 days.

(21) Appl. No.: 11/132,130

(22) Filed: May 17, 2005

(65) Prior Publication Data

US 2006/0003318 A1    Jan. 5, 2006

Related U.S. Application Data

(62) Division of application No. 10/651,141, filed on Aug. 28, 2003, now Pat. No. 6,893,814, which is a division of application No. 09/699,225, filed on Oct. 27, 2000, now Pat. No. 6,627,396.

(60) Provisional application No. 60/162,427, filed on Oct. 28, 1999.

(51) Int. Cl.
*G01N 33/53*    (2006.01)
*G01N 33/533*    (2006.01)
*C12Q 1/70*    (2006.01)

(52) U.S. Cl. .......................... 435/5; 435/7.71; 435/136; 436/546; 536/17.2

(58) Field of Classification Search ................... 435/5, 435/7.1, 136, 546; 536/17.2
See application file for complete search history.

(56) References Cited

U.S. PATENT DOCUMENTS 5,663,055 A * 9/1997 Turner et al. ................. 435/18

* cited by examiner

*Primary Examiner*—Long V. Le
*Assistant Examiner*—Shafiqul Haq
(74) *Attorney, Agent, or Firm*—Bruce H. Cottrell (57) ABSTRACT

A sensor for the detection of tetrameric multivalent neuraminidase within a sample is disclosed, where a positive detection indicates the presence of a target virus within the sample. Also disclosed is a trifunctional composition of matter including a trifunctional linker moiety with groups bonded thereto including (a) an alkyl chain adapted for attachment to a substrate, (b) a fluorescent moiety capable of generating a fluorescent signal, and (c) a recognition moiety having a spacer group of a defined length thereon, the recognition moiety capable of binding with tetrameric multivalent neuraminidase.

2 Claims, 2 Drawing Sheets

Prototype Receptor

*Fig. 1*

Ligand Neuraminidase Inhibitor

Spacer: Phosopho-(PEG)$_n$

Linker: Homoserine

Hydrophobic Fluorescent Reporter: BODIPY

Membrane Anchor: 2 C-18 Alkyl Chains

Prototype Receptor

*Fig. 2*

INFLUENZA SENSOR

RELATED APPLICATION

This application is a divisional of Ser. No. 10/651,141, filed Aug. 28, 2003, now U.S. Pat. No. 6,893,814 issued May 17, 2005 by Swanson et al. which is a divisional of Ser. No. 09/699,225, filed Oct. 27, 2000 now U.S. Pat. No. 6,627,396 issued Sep. 30, 2003 by Swanson et al.

BENEFIT OF PRIOR APPLICATION

This application claims the benefit of the filing date of U.S. Provisional Application 60/162,427, filed Oct. 28, 1999.

FIELD OF THE INVENTION

The present invention relates to a diagnostic sensor for the detection of influenza virus and to a method of detecting influenza virus with such a diagnostic sensor. This invention was made with government support under Contract No. W-7405-ENG-36 awarded by the U.S. Department of Energy. The government has certain rights in the invention.

BACKGROUND OF THE INVENTION

The early diagnosis of influenza infection is important for several reasons. One reason is that it is critical to be able to rapidly screen influenza from other infectious diseases in the event of a bio-agent attack. Most scenarios for bio-agent attacks show a slowed response to the recognition that an attack has taken place primarily because diseases such as anthrax and smallpox present flu-like symptoms. Medical personnel do not have a rapid and simple screen for influenza infection and, consequently, victims can be miss-diagnosed as having the flu and sent home. A delay of even a few days in the recognition of a bio-agent attack can have adverse affect on the minimization of the impact of an attack.

Another reason for a rapid diagnostic for influenza is important is in helping to avert a worldwide pandemic in the event that a new strain like the 1918 swine flu appears. Rapid screening with inexpensive fieldable sensors is essential to rapidly pinpoint a new potential outbreak. Although it is also important to specify the strain of the influenza infection, it is first critical to rapidly identify an outbreak and this can only be done using a flexible, inexpensive, fieldable sensor.

Recently, a number of high binding affinity neuraminidase (also known as sialidase) inhibitors have been developed and shown to be quite effective in curing the flu but only if such inhibitors are administered early on in the infection (generally within the first 24 to 48 hours). At present, these drugs can not be effectively used as there is not a simple diagnostic tool that can be used to detect the influenza virus early enough to effectively use neuraminidase inhibitors. The only technologies currently capable of early diagnosis of influenza are lab-based approaches like ELISA, which are instrument and personnel intensive, expensive, and slow. What is needed is a simple inexpensive diagnosis that can be easily used in either a clinical or field setting and yet have at least the same specificity and sensitivity as ELISA. Accordingly, it is highly desirable to develop a rapid diagnosis for influenza to facilitate the treatment of influenza using such neuraminidase inhibitors.

An optical biosensor system has recently been developed to rapidly detect protein toxins, e.g., cholera, shiga, and ricin (see, U.S. patent application Ser. No. 09/338,457, by Song et al., filed Jun. 22, 1999). The integrated optical biosensor developed for the detection of protein toxins was based on proximity-based fluorescence changes that are triggered by protein-receptor binding. In demonstrations of this approach for the detection of cholera and avidin using flow cytometry, it was shown that this technique was as sensitive as ELISA. In contrast to ELISA, such an optical biosensor can be much faster (minutes), simpler (a single step with no added reagents) and robust owing to the stability of the recognition molecules (glycolipids and biotin) and membranes. More recently, an optical biosensor system has been incorporated into planar optical waveguides (see, U.S. Provisional Patent Application Ser. No. 60/140,718, by Kelly et al., filed Jun. 22, 1999) and shown to have sensitivity equivalent to that of flow cytometry. The demonstration of such an optical biosensor using planar optical waveguides provides a path towards the development of miniaturized sensor arrays.

One object of the present invention is adaptation of such a biosensor to sensing applications directed to the detection of influenza virus.

Another object of the present invention is the selection and chemical modification of receptors that bind neuraminidase and that allow attachment of such receptors to membranes together with the incorporation of fluorophores.

SUMMARY OF THE INVENTION

To achieve the foregoing and other objects, and in accordance with the purposes of the present invention, as embodied and broadly described herein, the present invention provides for the detection of tetrameric neuraminidase within a sample, where a positive detection indicates the presence of a target virus within said sample, said sensor including a surface, recognition molecules situated movably at said surface, said recognition molecules capable of binding with said tetrameric multivalent neuraminidase, said recognition molecules further characterized as including a fluorescence label thereon, and, a means for measuring a change in fluorescent properties in response to binding between multiple recognition molecules and said tetrameric neuraminidase.

The present invention further provides a method of method of detecting tetrameric neuraminidase within a sample, where a positive detection indicates the presence of a target virus within said sample, said method including contacting a sample with a sensor including a surface, recognition molecules situated movably upon said surface, said recognition molecules capable of binding with said tetrameric multivalent neuraminidase wherein said recognition molecules include a fluorescence label thereon, and measuring a change in fluorescent properties in response to binding between multiple recognition molecules and said tetrameric neuraminidase.

The present invention further provides for the detection of tetrameric neuraminidase within a sample, where a positive detection indicates the presence of a target virus within said sample, said sensor including a surface, at least two different recognition molecules situated movably upon said surface, said recognition molecules capable of binding with said tetrameric multivalent neuraminidase wherein at least one recognition molecule includes a fluorescence donor label thereon and at least one recognition molecule includes a fluorescence acceptor label thereon, and, a means for measuring a change in fluorescent properties in response to binding between at least two different multiple recognition molecules and said tetrameric neuraminidase.

The present invention further provides a method of method of detecting tetrameric neuraminidase within a sample, where a positive detection indicates the presence of a target virus within said sample, said method including contacting a sample with a sensor including a surface, at least two different recognition molecules situated movably upon said surface, said recognition molecules capable of binding with said tetrameric multivalent neuraminidase wherein at least one recognition molecule includes a fluorescence donor label thereon and at least one recognition molecule includes a fluorescence acceptor label thereon, and measuring a change in fluorescent properties in response to binding between multiple recognition molecules and said tetrameric neuraminidase.

The present invention still further provides a trifunctional composition of matter including a trifunctional linker moiety including as groups bonded thereto (a) an alkyl chain adapted for attachment to a substrate, (b) a fluorescent moiety capable of generating a fluorescent signal, and (c) a recognition moiety having a spacer group of a defined length thereon, said recognition moiety capable of binding with tetrameric multivalent neuraminidase.

DETAILED DESCRIPTION

The present invention concerns a diagnostic sensor for the detection of influenza virus and to a method of detecting influenza virus with such a diagnostic sensor. In particular, the present invention concerns a diagnostic sensor capable of detecting organisms such as influenza virus that contain neuraminidase.

Organisms that contain neuraminidase include bacteria (*Vibrio cholerae, Clostridium perfringens, Streptococcus pneumoniae,* and *Arthrobacter sialophilus*) and viruses (influenza virus, parainfluenza virus, mumps virus, Newcastle disease virus, fowl plague virus, and sendai virus). In viruses, neuraminidase occurs as a tetrameric. This tetrameric structure facilitates the operation of the sensor of the present invention. Detection of neuraminidase activity related to any tetrameric neuraminidase structure in a virus is within the scope of the present invention. Detection of neuraminidase from influenza virus is particularly desired.

The selection of receptors is related to the prior work that has been done to synthesize neuraminidase inhibitors having high binding affinities. In principal, any neuraminidase inhibitor could be used but preferably the present influenza sensor will incorporate those neuraminidase inhibitors that have the highest binding affinities. Typically, neuraminidase inhibitor compositions having in vitro $K_i$ (inhibitory constants) of less than about $5 \times 10^{-6}$M, typically less than about $5 \times 10^{-7}$M and preferably less than about $5 \times 10^{-8}$M are excellent candidates for the recognition portion of the influenza sensor of the present invention.

In one embodiment, the influenza sensor of the present invention involves: 1) formation of a biomimetic membrane, which incorporates fluorescent dye-labeled receptors for neuraminidase, on the surface of an optical transducer (this could be a glass bead for flow cytometry-FCM—or a planar optical waveguide for an integrated optical biosensor); 2) the chemical modification of selected neuraminidase inhibitors to attach them to a membrane and to also attach fluorophores that fold into the fluid upper leaf of the membrane; 3) the detection, using a planar optical waveguide of a microsensor array or FCM, of envelope proteins or the influenza viral particle directly as measured by a shift in the ratios of intensity of two individual fluorescently-emitted signals, and 4) the use of multiple receptors in the recognition effect (in influenza neuraminidase is a tetramer) to insure extremely high effective binding affinities (avidity) and, as a result, ultrahigh sensitivities and specificities.

One advantage of the present invention is the ultrahigh sensitivity and specificity obtained by using multiple receptors each with high binding affinities (the avidity effect) to help insure early diagnosis, e.g., within the first 12 hours after infection. Another advantage of the present invention is the simplicity and speed of operation which makes detection fast and operation possible in a variety of situations. Another advantage of the present invention is the elimination of the need for additional reagents or additives thereby simplifying the use and extending shelf storage lifetimes. Another advantage of the present invention is the flexibility in adaptation to either flow cytometry or to miniaturized sensor systems utilizing planar optical waveguide permits use in a variety of clinical or field situations. Another advantage of the present invention is the robustness of the sensor system that results from the high stability of the receptor molecules and the active membrane. Another advantage of the present invention is the simplicity of sample introduction which minimizes front-end sample preparation.

Coupling recognition to signal transduction and amplification can be conducted as follows. The sensor of the present invention mimics many cell signaling processes in nature by directly coupling a recognition event to signal transduction and amplification. In the case of the present influenza sensor, the sensor relies on recognition of chemically modified sialic acid-like receptors by neuraminidase, an envelope protein for influenza. As neuraminidase in a virus such as influenza is a multivalent protein (neuraminidase is a tetramer), binding will bring several receptors into close proximity thereby triggering proximity based fluorescence changes. The selection of target receptors is discussed below. The receptor molecules are chemically modified to both attach fluorescent tags and to attach them to the fluid upper leaf of a phospholipid bilayer. The choice of a phospholipid bilayer is important for several reasons. First, this is an excellent mimic of a cell membrane surface, which is the natural target of envelope viruses. Second, the use of membrane mimics helps minimize non-specific protein absorption and the attendant nonspecific response of the sensor element. Third, the upper leaf of the membrane is fluid thereby insuring that the receptor molecules and their fluorescent tags are mobile and, if the concentration is low, relatively distant thereby minimizing proximity based fluorescence changes prior to protein binding. The binding event between neuraminidase and the sialic acid-like receptors then brings multiple receptors into close proximity triggering the fluorescence changes. There are two proximity based fluorescence changes that can be used for detection. The simplest is self-quenching of fluorescence that results in a sharp decrease in the fluorescence of the fluorophore attached to the receptor molecules. The second is resonant energy transfer (FRET) where donor fluorophores transfer their energy to the acceptor fluorophores that are attached to the receptor molecules. In this case, the receptor molecules are tagged with both fluorescent donors and acceptors (typically in a 1:1 ratio). FRET results in a color change in the fluorescence, which can be more easily distinguished from simple self-quenching in terms of being directly coupled to the receptor-protein recognition. Preferably, the selection of fluorophores is such that there must be overlap of the donor emission with the excitation profile of the acceptor. Many pairs of fluorophores exhibit this relationship and the selection is primarily dictated by the stability of the fluorophores and the most effective separation of the emission profiles to minimize background fluorescence.

Influenza is an RNA virus and, therefore, has a rapid antigenic drift and antigenic shift. As a result, the binding of antibodies and receptor molecules to neuraminidase is constantly changing even within a particular strain. However, antigenic shift and drift do not affect binding of a neuraminidase inhibitor which bind to silacic acid. For this reason, the present invention has targeted the binding region of neuraminidase that targets sialic acid residues on the cell membrane surface. It is through neuraminidase binding to sialic acid that the influenza virus particle invades the host cell through membrane fusion. As this binding event is critical to viral particle invasion, it is likely that the binding pocket in neuraminidase that selects sialic acid is relatively invariant. There have been several crystal structures of neuraminidase measured with differing inhibitors (molecules that mimic sialic acid but which have even higher binding affinities to neuraminidase) that show the binding pocket for sialic acid site is relatively invariant. Moreover, there has been a great deal of work in synthesizing neuraminidase inhibitors that have exceptionally high binding affinities and these molecules are all good potential receptors for the influenza sensor of the present invention. As noted below, initial selection was of a few molecules that have binding affinities in the micromolar range. The use of molecules that target the sialic acid binding site insures that this sensor will be effective over a long period of time and to virtually any strain of influenza. Moreover, as neuraminidase is multivalent with regard to binding sialic acid, the use of inhibitors and sialic acid variants insures that the above sensor transduction scheme (proximity based fluorescence changes) can work and, equally important, that the effective binding affinities are high by virtue of the avidity effect.

Chemical modification of the neuraminidase receptors can be as follows. A number of neuraminidase inhibitors derived from 3,4-diamino benzoic acid have been described in the literature. These compounds bind to the sialic acid binding site on neuraminidase. One of these 3,4-diamino benzoic acid-based neuraminidase inhibitors, 4-acetylamino-3-guanidine benzoic acid is reported to bind NA with an affinity constant of $10^5$. The present approach to a neuraminidase detector involves covalently linking this inhibitor to a fluorescent molecule that is anchored into a membrane. The covalent attachment is accomplished as follows. 3,4-Diamino benzoic acid (I) is acetylated on the 4-amino group to yield 3-amino-4-acetylamino benzoic acid (II). Compound II is then alkylated to yield 3-alkylamino-4-acetylamino benzoic acid (III). Treatment of III with cyanogen bromide followed by ammonia yield compound IV that may serve as a neuraminidase receptor in the present invention.

The neuraminidase receptor (IV) can be linked to the fluorescent probe a number of ways. One possible approach is as follows. First compound IV is attached to a polyethylene glycol spacer to the alpha-amino group of lysine. The alpha-carboxyate is modified as an amide to a 16, 17, or 18-carbon hydrocarbon, which serves as a membrane anchor. The ε-amino group of lysine is modified to carry a hydrophobic fluorescent molecule such as a Bodipy molecule.

Preparation of the Membrane Architectures on Optical Transducers can be as follows. As noted above, the receptor molecules would have been chemically modified to bind them into the upper leaf of a phopholipid bilayer through attachment to two aliphatic side chains. Moreover, the fluorophore has been selected and attached in a way that insures that it folds over into the upper leaf of the bilayer. The fact that the fluorophore resides in the upper leaf of the bilayer is important for two reasons. First, this insures that the fluorophore itself and the linker that attaches it to the lipid tail do not interfere with recognition by providing a non-specific site for protein binding. Second, the residence of the fluorophore in the upper leaf provides additional stability of the receptor-membrane structure. The membranes are then fabricated onto optical transducers (either glass beads for FCM or planar optical waveguides for microsensor arrays) by vesicle fusion onto hydrophobic or hydrophilic surfaces. The simplest approach is vesicle fusion onto a hydrophilic surface to form a support bilayer. This can be done in a flow cell where the surface can be exposed for a period of time (hours) to a solution containing the vesicles. The second approach is to spread vesicles containing the tagged receptors over a methyl terminated self-assembled monolayer to form a hybrid bilayer where the lower leaf is covalently attached to the transducer surface. The hybrid bilayer has the advantage of better long-term stability.

In the present invention, the architecture of the fluid membranes can be as a regular bilayer membrane where both layers are deposited upon a support surface, can be a hybrid bilayer, e.g., where a first layer is covalently attached to an oxide surface, can be a selectively tethered bilayer on an oxide surface, where a membrane molecule is covalently bonded to the oxide substrate, or a bilayer cushioned by a polymer film. Supported membranes useful in the practice of the present invention are generally described by Sackmann, in "Supported Membranes: Scientific and Practical Applications", Science, vol. 271, no. 5245, pp. 43–45, Jan. 5, 1996. Hybrid bilayer membranes or selectively tethered bilayer membranes may be more preferred as such membranes may have greater stability over time and therefor provide greater shelf lifetimes for sensor applications. Additionally, a surface with mobile receptors such as an oxide surface with mobile receptor molecules thereon can serve as a platform in the present invention.

Bilayer membranes can be formed upon a planar oxide substrate, e.g., by initially forming vesicles followed by vesicle fusion or spreading of, e.g., phospholipid, bilayers on glass substrates as is well known to those skilled in the art.

In one embodiment of the present invention, the transduction element used is fluorescein, which has a high extinction coefficient, a high fluorescence quantum yield and proximity-dependent fluorescence self-quenching. Other suitable fluorescent dyes are well known to those of skill in the art. Fluorescein may be covalently attached to a free functional group by appropriate coupling to produce a fluorescein-labeled moiety. The fluorescein should have minimal influence on the binding affinity of the recognition portion of the final molecule to the influenza virus.

In another embodiment of the present influenza sensor, the sensing molecules can be functionalized with either an acceptor dye molecule or a donor dye molecule whose excitation spectra overlap for efficient energy transfer. In effect, excitation of a blue emitting dye can result in fluorescence with a maximum at roughly 570 nm when functionalized Bodipy is free to move about in the bilayer membrane. Upon exposure to influenza virus (tetrameric neuraminidase), both the donor and the acceptor dyes are brought into close proximity. This can result in an energy transfer and a decrease in the fluorescence at 570 nm and a concomitant increase in the fluorescence of the acceptor dye that has its fluorescence maximum at roughly 630 nm. Such a simultaneous increase in the red fluorescence and decrease in the blue fluorescence is a highly distinguishing feature of this sensor approach. In effect, a two-color fluorescence measurement can be used to probe the intensity of fluorescence from both dye molecules. Only a specific binding event between the neuraminidase and the receptor will give rise to such a simultaneous increase in one fluorescent signal with a decrease in the other. Any change in the environment will give rise to shifts of the fluorescence of both dye molecules. Such an energy transfer approach provides a means for self-referencing in such sensor applications.

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

Figure 1:
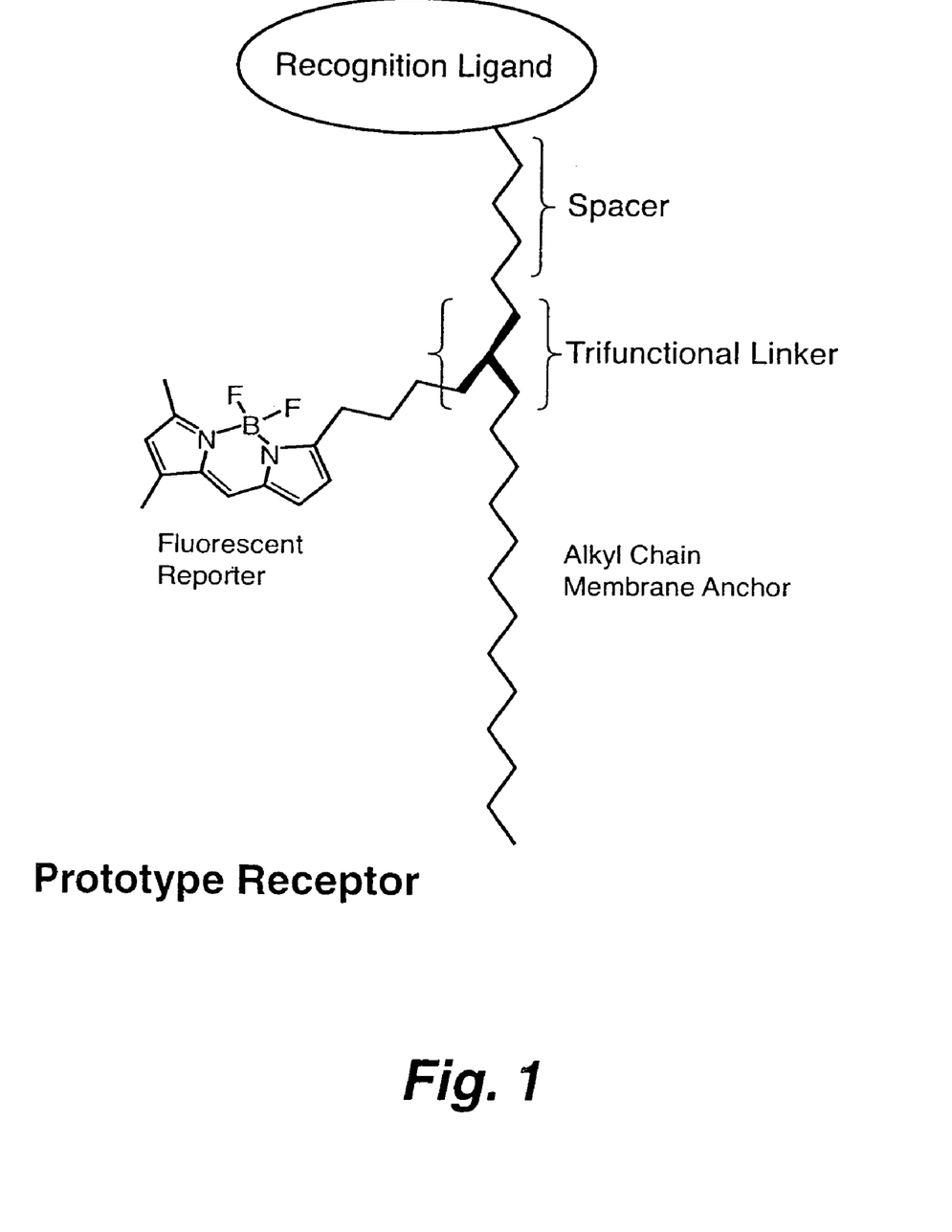
FIG. 1 shows a diagram of an exemplary receptor molecule including the three necessary functionalites.

As discussed in this application, in a preferred embodiment the signal transduction scheme is dependent of FRET. To be detected, influenza virus particles (neuraminidase tetramers) must bind two or more receptor molecules. Binding must cause the receptors to aggregate resulting in fluorescence energy transfer. These "receptor molecules" have three functions. First they must have a recognition ligand that binds specifically to an agent. The receptor must carry the fluorescent reporter and must be mobile in a lipid bilayer membrane. Diagrammed in FIG. 1 is a prototype "receptor". A trifunctional linker molecule must connect the recognition site, fluorescent reporter, and membrane anchor.

Scheme 1

Trifunctional Linker—Because they are available, α-amino acids with functional groups on the side chains are good candidates as trifunctional linkers. In addition to the α-amino and α-carboxyl functional groups, common amino acids are available with hydroxyl (serine), carboxyl (glutamate and aspartate), thiol (cysteine) and amino (lysine) functionality in the side chain. Lysine derivatives are available with the α-amino and ε-amino groups differentially blocked so their chemistry is orthoganal. Influenza receptors are prepared from commercial $N^\alpha$-benzyloxycarbonyl-$N^\epsilon$-butyloxycarbonyl-L-lysine N-hydroxysuccinimide ester (1, Z-Lys(Boc)-Osu). The $N^\alpha$- and $N^\epsilon$-blocking groups are removed differentially by hydrogenation (CBZ) or dilute acid hydrolysis (Boc). The alkyl anchors are added first by displacement of the N-hydroxy-succinimide ester by treatment of Z-Lys(Boc)-Osu with distearylamine (2, Scheme 1). Next the CBZ group is removed by hydrogenation under standard conditions. Dialkyl-substituted amide (4) have been prepared in essentially quantitative yield as the starting material for the synthesis of the artificial influenza receptors described here. Recognition ligand is attached through a spacer to the α-amino group. Next the Boc protecting group is removed and the fluorescent probe attached to the ϵ-amino group.

The neuraminidase in influenza virus is uniquely a homotetrameric protein. An active site-specific binder of neuraminidase would provide a flu-specific detector using the FRET scheme. Each viral particle contains several hundred copies of the neuraminidase tetramer. In addition, many competitive inhibitors of flu neuraminidase have been developed as anti-viral agents. These inhibitors provide a specific probe for the active site of neuraminidase. One example, 4-acetylamino-3-guanidino benzoic acid (11) binds flu neuraminidase with a 10 micromolar (μm) affinity constant (Sudbeck et. al., Journal of Molecular Biology, vol. 267, pp. 584–594 (1997)). Derivatives of these compounds have been prepared that will be linked to the receptor through either 4-amino function or the 3-guanidino group. Other nmolar inhibitors are also becoming available from the pharmaceutical industry.

Among the numerous neuraminidase inhibitors taught by the prior art are thoose compounds described by Luo et al., in U.S. Pat. No. 5,453,533, by Bischofberger et al., in U.S. Pat. No. 5,763,483, by Bischofberger et al., in U.S. Pat. No. 5,952,375, Bischofberger et al., in U.S. Pat. No. 5,958,973, Kim et al., in U.S. Pat. No. 5,512,596, Kent et al., in U.S. Pat. No. 5,886,213, Babu et al., in U.S. Pat. No. 5,602,277, by von Izstein et al., in U.S. Pat. No. 5,360,817, Lew et al., in U.S. Pat. No. 5,866,601, by Babu et al., in WO97/47194A1, by Babu et al., in WO99/33781A1, and by Brouillette et al., in WO99/14191A1. Each of these various neuraminidase inhibitors may be structurally incorporated into the influenza sensor of the present invention. The various neuraminidase inhibitors taught by these enumerated patents are incorporated herein by reference.

Many of the neuraminidase inhibitors having the highest binding affinities include at least one functionality from among carboxylate, guanidinium and N-acetyl groups.

Scheme 2

Scheme 2 shows the synthesis of the neuraminidase ligand linked via the guanidino group. Commercially available 4-amino benzoic acid (5) is converted to its methyl ester (6) by treatment with methanol/HCl. Such a methylation is described by Haslam, Tetrahedron, 1980, 36, 2409. Methyl 4-amino benzoic acid (6) is treated with acetic anhydride to yield methyl 4-acetylamino benzoic acid (7). Such a treatment is described by Greene, T. W., "Protective Groups in Organic Synthesis" (John Wiley & Sons, New York, 198.1), in particular at pages 251–252. Treatment of (7) with one equivalent of nitronium tetrafluoroborate in methylene chloride yields methyl 3-nitro-4-acetylamino benzoic acid (8). Such a treatment is described by Ottoni et al., Tetrahedron Lett. (1999), 40(6), 1117. Hydrogenation of (8) over Pd/C in ethanol yields the methyl 3-amino-4-acetylamino benzoic acid (9). Such a hydrogenation is described by Entwistle et al., J. Chem. Soc., Perkin Trans 1, 1977, 433. Product 9 is alkylated with one equivalent of a spacer molecule where n is generally from about 2 to about 6. Such a alklyation is described by Onaka et al., Chem. Lett., 1982, 11, 1783. The secondary amine is then converted to the guanidino function by treatment with cyanogen bromide followed by ammonia yielding compound 11. Such a conversion is described by Rai et al., Indian J. Chem., Sect. B, 1976, 14B(5), 376; by Pankratov et al., Izv. Akad. Nauk SSSR, Ser. Khim. 1975, 10, 2198; and by March, "Advanced Organic Chemistry, 4th edition", (John Wiley & Sons, New York, 1992), in particular at page 903. A fluorescent group is then added to this ligand using the steps below.

The recognition ligand (11) is then attached via the spacer to the lipid anchor as outlined in Scheme 3. The free carboxylate on the spacer of compound 11 is attached to the α-amino group of the lysine linker (4) with dicyclohexyl carbodiimide using standard peptide synthesis conditions to yield (13). Such a process is described by March, "Advanced Organic Chemistry, 4th edition", (John Wiley & Sons, New York, 1992), in particular at page 420. The methyl ester is saponified from 13 by treatment with lithium hydroxide in THF/water to yield (14). Such a process is described by March, "Advanced Organic Chemistry, 4th edition", (John Wiley & Sons, New York, 1992), in particular at page 383. Facile removal of the Boc group from (14) with trifluoroacetic acid is required before introduction of the fluorescent group. Such a process is described by March, "Advanced Organic Chemistry, 4th edition", (John Wiley & Sons, New York, 1992), in particular at page 168. The BODIPY fluorophors are available as their N-hydroxysuccinimide esters. Displacement of the O-Su ester with the α-amino group of the lysine linker will yield the final influenza receptor (Scheme 4).

Scheme 3

12

13

14

-continued

15

Scheme 4 shows the synthesis of a neuraminidase ligand linked via the 4-amino group of the 4-acetylamino-3-guanidino benzoic acid-based inhibitors. Methyl 4-amino benzoic acid (6) is used as the starting material. Treatment of 6 with the acyl chloride 16 yields the amide 17. The 3-amino function is added by treatment of 17 with nitronium tetrafluoroborate followed by hydrogenation as described in scheme 2. Conversion of the amino function into a guanidino group is accomplished by treatment with cyanogen bromide followed by ammonia. The terminal hydroxyl on the spacer of compound 20 must be oxidized to a carboxylate for attachment to the lysine linker. The free carboxylate on amino-linked neuraminidase ligand (21) is attached to the α-amino group of the lysine linker (4) with dicyclohexyl carbodiimide as described in scheme 3.

Within the context of the invention samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces neuraminidase, frequently a pathogenic organism such as a virus. Samples can be contained in any medium including water and organic solvent/water mixtures. Samples include living organisms such as humans, and man made materials such as cell cultures.

Figure 2:
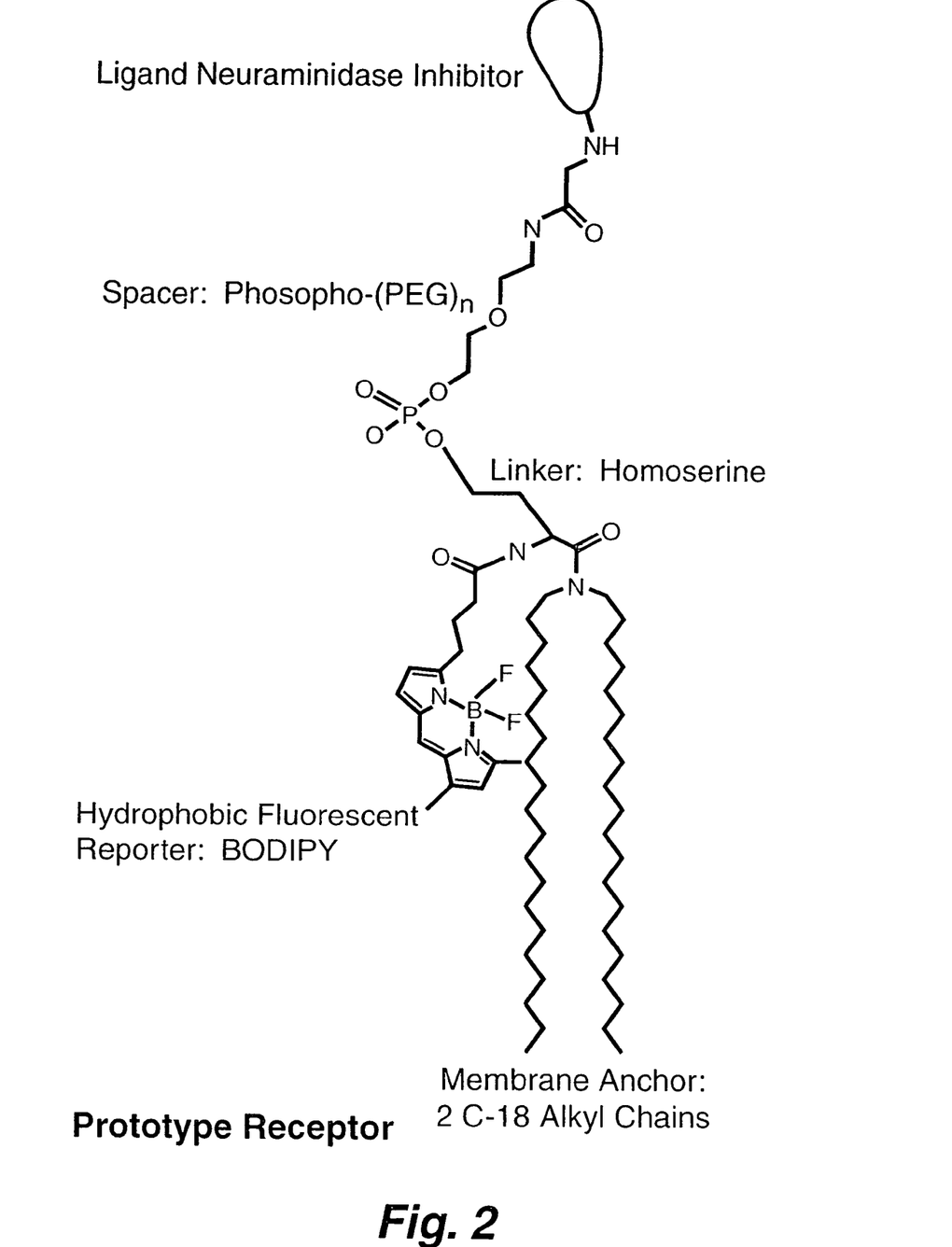
FIG. 2 shows a diagram of another exemplary receptor molecule including the three necessary functionalites.

In another embodiment, a varied synthesis of the generic linker molecule can be conducted. As discussed above the signal transduction scheme is dependent on FRET induced by aggregation of two or more fluorescently tagged antibodies bound to a common surface. These "receptor molecules" have three functions. First, they must have a recognition ligand that binds specifically to an agent. For detection of influenza, the recognition ligands can be any neuraminidase inhibitors. In addition, the receptor must carry the fluorescent reporter and must be mobile in a lipid bilayer membrane. Diagrammed in FIG. 2 is a prototype "receptor". Synthetic schemes to prepare the this receptor are diagrammed in schemes 5–6. A trifunctional linker molecule, homoserine connects the recognition ligand, fluorescent reporter, and membrane anchor. Based on results obtained in developing a cholera sensor, this prototype receptor has the following design characteristics. It has two C-18 alkyl chains needed to tightly anchor the receptor in the membrane. The fluorescent reporters are BODIPY-dyes, which are hydrophobic and tethered to the receptor so as to allow the dye to insert into the lipid bilayer. Insertion into the fluid upper leaf of the bilayer shields the dye molecule from non-specific protein-dye interactions, provides long term stability towards hydrolysis and helps to anchor the antibody to the membrane. The phosphoryl (PEG)$_n$-spacer will partition into the aqueous phase and has been extensively studied for use as in preparing bio-compatible surfaces. PEG is known to minimize non-specific protein-surface interactions.(see literature references 20, 23, 27, 41, and 55–57) The length of the spacer can be adjusted by adding more PEG monomers to optimize fluorescent energy transfer and binding.

The synthesis of the prototype receptor is outlined in detail in schemes 5 and 6. For each step literature references are included and the list of references is below. In addition, yields are included for some steps. Homoserine was chosen as the trifunctional linker because is not subject to—elimination as is serine. Two routes are being explored to link the spacer to homoserine through either a phospodiester or a sulfone. Both of the phosphate and sulfone groups are expected to partition into the aqueous phase. While the phosphodiester linkage is more similar to phospholipids, the potential advantage of the sulfone is its stability to hydrolysis. A common intermediate in both routes is compound IV. Commercially available, N-Fmoc O-Trityl homoserine (I) was coupled to dioctadecylamine (II) using standard peptide coupling conditions to incorporate the membrane anchors (FIG. 2).(see literature references 3, 12, 29, and 53) Removal of the trityl-protecting group with trifluoroacetic acid frees the hydroxymethyl group of homoserine (IV) for addition of the spacer.(4-6)

Garegg, et. al. 1987; Andrews, et. al. 1991; Staerkaer, et. al. 1991; De Bont, et. al. 1990

VII

Ward, et. al. 2000; Kropp, et. al. 2000; Greenhalgh, 1992; Trost and Braslau, 1988; Evans and Grade. 1986

VIIa

In the phosphodiester route, treatment of homeserine (IV) with $(tBuO)_2P(N(iPr)_2)$ in the presence of tetrazole follow by deblocking with trifluoroacetic acid gave the phospho homoserine derivative (V) in an overall yield of 73%.(see literature references 33, 37–39, 46, 50, 51, and 54) Standard phosphonate DNA synthesis conditions were used for the condensation of the PEG spacer (VI) with the phospo homoserine (V).(see literature references 9, 10, and 40) Oxidation with t-butyl hodroperoxide yielded the phosphodiester (VII).(see literature references 2, 17, 21, and 43) The intermediate VII has been prepared, purified and characterized by NMR spectroscopy (overall yield 60%). In the sulfone route, conversion the hydroxyl group of homoserine to its corresponding bromide (Va) was achieved in 73% yield by treatment with triphenyl phosphine and carbon tetrabromide.(see literature references 26, 28, and 49) Nucleophilic substitution of bromide by a thiol-terminated PEG spacer (VIa) (18, 48) followed by oxidation will give the sulfone (VIIa).(see literature references 19, 22, 30, 44, and 52).

To complete the linker, the terminal amino group on the PEG spacer is freed, a thiol carboxy, amino, or aldehyde reactive group is added and then the BODIPY dye is added. As diagrammed in scheme 5, this scheme is depicted only for the phopodiester-linked receptor. The identical scheme will be carried out on VIIa to finish the sulfone-linked receptor. First, the BOC-amino protecting group is removed from VII under acidic conditions.(see literature references 4–6) Next reactive group for specific linkage to recognition ligands is added to the PEG-terminal amino group. For example, a thiol specific disulfide(see literature reference 11) or maleimide derivative(see literature reference 32) is added to react with a free thiol on the neuraminidase inhibitor. Similarly, an aldehyde specific hydrazone is added to react with the reducing terminal sugar on a sialaic acid containing oligosaccharide.(see literature references 16, 31, 35, and 36)

Scheme 6
Synthesis of prototype receptor. References are given for each step. The ligand specific reactive groups (R) are diagrammed below and are available commersvially as their N-hydroxysuccinimide esters.

These reagents, diagrammed in FIG. 4, are available as activated N-hydroxysuccinimide esters (Pierce Chemical Co.) (see literature references 1, 7, 45, and 47), which will react directly with the free amino group to form an amide linkage.(see literature references 8, 25, and 34) The BODIPY dye is added in "one pot step" involving removal of the Fmoc group from the homoserine amino group,(see literature references 13–15) which will be modified with the N-hydroxsuccinimide esters of one of the BODIPY dyes. (see literature references 24 and 42) DCC is dicyclohexyl-carbodiimide. HOBT is 1-hydroxybenzotriazole. DEAD is diethyl azodicarboxylate. TFA is trifluoroacetic acid.

Representative reactive groups for the attachment of the ligand

Sulfhydrylreactive
Carisson, et. al., 1978

Sulfhydrylreactive
Lewis and Shively 1998;
Bieniariz et. al., 1996; Ali
and Quadri, 1996; Uto, et.
al., 1991 nonspecific photoactivated
van der Horst et. al., 1990;
Wood and O'Dorsio 1985

-continued carbohydrate specific
hydrazone
O'Shannessy and Quarles, carbohydrate
specific
hydrazone
Chamow, 1992 carbohydrate specific
aldehyde reactive
Lemaitre, et. al., 1987;
Peng. et. al., 1987; Van 1. Ali, M. S., and S. M. Quadri. 1996. Maleimido Derivatives of Diethylenetriaminepentaacetic acid and Triethylenetetra-aminehexaacetic Acid: Their synthesis and potential for specific conjugation with biomolecules. Bioconjugate Chem. 9:645–654.
2. Andrews, D. M., J. Kitchin, and P. W. Seale. 1991. Solid-phase synthesis of a range of O-phosphorylated peptides by post-assembly phosphitylation and oxidation. Int. J. Pept. Protein Res. 38(5):469–475.
3. Atherton, E., and R. C. Sheppard. 1989. Solid phase peptide synthesis—a practical approach. IRL Press, Oxford.
4. Barlos, K, D. Gatos, O. Chatzi, S. Koutsogianni, and W. Schaefer. 1993. Solid phase synthesis using trityl type side chain protecting group. Pept. 1992, Proc. Eur. Pept. Symp. 22nd:283–284.
5. Barlos, K, D. Gatos, S. Koutsogianni, W. Schafer, G. Stavropoulos, and Y. Wenqing. 1991. Preparation and application of N-Fmoc-O-Trt-hydroxy amino acids for solid-phase synthesis of peptides. Tetrahedron Lett. 32(4): 471–474.
6. Barlos, K., P. Mamos, D. Papaioannou, S. Patrianakou, C. Sanida, and W. Schaefer. 1987. Application of the Trt and Fmoc groups for the protection of polyfunctional a-amino acid. Liebigs Ann. Chem. 12:1025–1030.
7. Bieniariz, C., M. Husain, G. Barnes, C. A. King, and C. J. Welch. 1996. Extended length heterofunctional coupling agents for protein conjugations. Bioconjugate Chem. 7:88–95.
8. Briggs, M. S. J., I. Bruce, J. N. Miller, C. J. Moody, A. C. Simmonds, and E. Swann. 1997. Synthesis of functionalized fluorescent dyes and their coupling to amines and amino acids. J. Chem. Soc. Perkin Trans. 1.7:1051–1058.
9. Campbell, D. A. 1992. The synthesis of phosphonate esters; an extension of the Mitsunobu reaction. J. Org. Chem. 57(23):6331–6335.
10. Campbell, D. A., and J. C. Bermak. 1994. Phosphonate Ester Synthesis Using a Modified Mitsunobu Condensation. J. Org. Chem. 59(3):658–660.
11. Carlsson, J., H. Drevin, and R. Axen. 1978. Protein thiolation and reversible protein—protein conjugation. N-succinimidyl-3-(2-pyridyldithio)propionate, a new heterobifunctional reagent. Biochem. J. 173:723–737.

12. Carpino, L. A. 1993. 1-Hydroxy-7-azabenzotriazole. An efficient peptide coupling additive. J. Am. Chem. Soc. 115(10):4397–4398.
13. Carpino, L. A. 1987. The 9-fluorenylmethyloxycarbonyl family of base-sensitive amino-protecting groups. Acc. Chem. Res. 20(11):401–407.
14. Carpino, L. A., and G. Y. Han. 1972. 9-Fluorenylmethoxycarbonyl amino-protecting group. J. Org. Chem. 37(22):3404–3409.
15. Carpino, L. A., E. M. E. Mansour, C. H. Cheng, J. R. Williams, R. MacDonald, J. Knapczyk, M. Carman, and A. Lopusinski. 1983. Polystyrene-based deblocking-scavenging agents for the 9-fluorenylmethyloxycarbonyl amino-protecting group. J. Org. Chem. 48(5):661–665.
16. Chamow, S. M., T. P. Kogan, D. H. Peers, R. A. Byrn, and A. Askenaszi. 1992. Conjugation of soluble CD4 without loss of biological activity via a novel carbohydrate-directed crosslinking reagent. J. Biol. Chem. 267(22):15917–15922.
17. De Bont, H. B. A., J. H. Van Boom, and R. M. J. Liskamp. 1990. Automatic synthesis of phosphopeptides by phosphorylation on the solid phase. Tetrahedron Lett. 31(17):2497–2500.
18. Easton, C. J., and S.C. Peters. 1990. Synthesis of novel crosslinked amino acid derivatives. Aust. J. Chem. 43(1):87–97.
19. Evans, T. L., and M. M. Grade. 1986. Phase-transfer-controlled selective oxidation of diaryl sulfides to diaryl sulfoxides using potassium hydrogen persulfate. Synth. Commun. 16(10):1207–1216.
20. Feldman, K, G. Haehner, N. D. Spencer, P. Harder, and M. Grunze. 1999. Probing Resistance to Protein Adsorption of Oligo(ethylene glycol)-Terminated Self-Assembled Monolayers by Scanning Force Microscopy, p. 10134–10141, J. Am. Chem. Soc., vol. 121.
21. Garegg, P. J., T. Regberg, J. Stawinski, and R. Stroemberg. 1987. Studies on the oxidation of nucleoside hydrogen phosphonates. Nucleosides Nucleotides. 6(1–2):429–432.
22. Greenhalgh, R. P. 1992. Selective oxidation of phenyl sulfides to sulfoxides or sulfones using Oxone and wet alumina. Synlett. 3:235–236.
23. Harder, P., M. Grunze, R. Dahint, G. M. Whitesides, and P. E. Laibinis. 1998. Molecular Conformation in Oligo (ethylene glycol)-Terminated Self-Assembled Monolayers on Gold and Silver Surfaces Determines Their Ability To Resist Protein Adsorption, p. 426–436, J. Phys. Chem. B, vol. 102.
24. Hung, S.C., R. A. Mathies, and A. N. Glazer. 1998. Comparison of Fluorescence Energy Transfer Primers with Different Donor-Acceptor Dye Combinations. Anal. Biochem. 255(32).
25. Jo, S., P. S. Engel, and A. G. Mikos. 2000. Synthesis of poly(ethylene glycol)-tethered poly(propylene fumarate) and its modification with GRGD peptide. Polymer. 41(21):7595–7604.
26. Katritzky, A. R., B. Nowak-Wydra, and C. M. Marson. 1987. The preparation of synunetrical secondary alkyl bromides. Chem. Scr. 27(3):477–478.
27. Kenausis, G. L., J. Voeroes, D. L. Elbert, N. Huang, R. Hofer, L. Ruiz-Taylor, M. Textor, J. A. Hubbell, and N. D. Spencer. 2000. Poly(L-lysine)-g-Poly(ethylene glycol) Layers on Metal Oxide Surfaces: Attachment Mechanism and Effects of Polymer Architecture on Resistance to Protein Adsorption. J. Phys. Chem. B. 104(3298–3309).
28. Kocienski, P. J., G. Cernigliaro, and G. Feldstein. 1977. Pheromone synthesis. 4. A synthesis of (±)-methyl n-tetradeca-trans-2,4,5-trienoate, an allenic ester produced by the male dried bean beetle Acanthoscelides obtectus (Say). J. Org. Chem. 42(2):353–355.
29. Konig, W., and R. Geiger. 1970. A new method for synthesis of peptides: activation of the carboxyl group with dicyclohexylcarbodiimide using 1-hydroxybenzotriazoles as additives. Chem. Ber. 103(3):788–798.
30. Kropp, P. J., G., W. Breton, J. D. Fields, J. C. Tung, and B. R. Loomis. 2000. Surface-Mediated Reactions. 8. Oxidation of Sulfides and Sulfoxides with tert-Butyl Hydroperoxide and OXONE. J. Am. Chem. Soc. 122(18):4280–4285.
31. Lemaitre, M., B. Bayard, and B. Lebleu. 1987. Specific antiviral activity of a poly(L-lysine)-conjugated oligodeoxyribonucleotide sequence complementary to vesicular stomatitis virus N protein mRNA initiation site. Proc. Natl. Acad. Sci. U.S.A. 84(3):648–652.
32. Lewis, M. R., and J. E. Shively. 1998. Maleimidocysteineamido-DOTA-derivatives new reagents for radiometal chelate conjugation to antibody sulfhydryl groups undergo pH-dependent clevage reactions. Bioconj. Chem. 9:72–86.
33. Lindh, I., and J. Stawinski. 1989. A general method for the synthesis of glycerophospholipids and their analogs via H-phosphonate intermediate. J. Org. Chem. 54(6):1338–1342.
34. Morpurgo, M., E. A. Bayer, and M. Wilchek. 1999. N-hydroxysuccinimide carbonates and carbamates are useful reactive reagents for coupling ligands to lysines on proteins' J. Biochem. Biophys. Methods. 38(1):17–28.
35. O'Shannessy, D. J., and R. H. Quarles. 1985. Specific conjugation reactions of the oligosaccharide moieties of immunoglobins. J. Applied Biochem. 7(347–355).
36. Peng, L., G. J. Calton, and J. W. Burnett. 1987. Effect of borohydride reduction on antibodies. Appl. Biochem. Biotechnol. 14:91–99.
37. Perich, J. W., P. F. Alewood, and R. B. Johns. 1986. Solution-phase synthesis of an O-phosphoseryl-containing peptide using phenyl phosphorotriester protection, p. 1373–6, Tetrahedron Lett., vol. 27.
38. Perich, J. W., and E. C. Reynolds. 1991. Fmoc/solid-phase synthesis of Tyr(P)-containing peptides through t-butyl phosphate protection, p. 572–5, Int. J. Pept. Protein Res., vol. 37.
39. Perich, J. W., R. M. Valerio, and R. B. Johns. 1986. Solid-phase synthesis of an O-phosphoseryl-containing peptide using phenyl phosphorotriester protection, p. 1377–80, Tetrahedron Lett., vol. 27.
40. Saady, M., L. Lebeau, and C. Mioskowski. 1995. Direct esterification of phosphonic acid salts using the Mitsunobu reaction. Synlett. 6:643–644.
41. Seigel, R. R., P. Harder, R. Dahint, M. Grunze, F. Josse, M. Mrksich, and G. M. Whitesides. 1997. Online Detection of Nonspecific Protein Adsorption at Artificial Surfaces, p. 3321–3328, Anal. Chem., vol. 69.
42. Song, X., and B. I. Swanson. 1999. Direct, Ultrasensitive, and Selective Optical Detection of Protein Toxins Using Multivalent Interactions, p. 2097–2107, Anal. Chem., vol. 71.
43. Staerkaer, G., M. H. Jakobsen, C. E. Olsen, and A. Holm. 1991. Solid phase peptide synthesis of selectively phosphorylated peptides. Tetrahedron Lett. 32(39):5389–5392.
44. Trost, B. M., and R. Braslau. 1988. Tetra-n-butylammonium oxone. Oxidations under anhydrous conditions. J. Org. Chem. 53(3):532–537.

45. Uto, I., T. Ishimatsu, H. Hirayama, S. Ueda, J. Tsuruta, and T. Kambara. 1991. Determination of urinary Tamm-Horsfall protein by ELISA using a maleimide method for enzyme-antibody conjugation. J. Immunol. Meth. 138: 87–94.
46. Valerio, R. M., A. M. Bray, N. J. Maeji, P. O. Morgan, and J. W. Perich. 1995. Preparation of O-phosphotyrosine-containing peptides by Fmoc solid-phase synthesis: evaluation of several Fmoc-Tyr(PO3R2)—OH derivatives. Lett. Pept. Sci. 2(1):33–40.
47. van der Horst, G. T. J., G. M. S. Mancini, R. Brossmer, U. Rose, and F. W. Verheijen. 1990. Photoaffinity labeling of a bacterial sialidase with an aryl azide derivative of sialic acid. J. Biol. Chem. 265(19):10801–10804.
48. Verny, M., and C. Nicolas. 1988. [3H]-Labeling of hydroxyethyl groups—synthesis of S-(2-hydroxy-[2–3H]-ethyl)glutathione and of [3H]melphalan. J. Labelled Compd. Radiopharm. 25(9):949–955.
49. Wagner, A., M. P. Heitz, and C. Mioskowski. 1989. Direct conversion of tetrahydropyranylated alcohols to the corresponding bromides. Tetrahedron Lett. 30(5): 557–558.
50. Wakamiya, T., K. Saruta, S. Kusumoto, S. Aimoto, K. Yoshizawa-Kumagaye, and K. Nakajima. 1993. Synthetic study of phosphopeptides by solid-phase method. Pept. Chem. 31:17–20.
51. Wakamiya, T., K. Saruta, J. Yasuoka, and S. Kusumoto. 1994. An efficient procedure for solid-phase synthesis of phosphopeptides by the Fmoc strategy. Chem. Lett. 6:1099–1102.
52. Ward, R. S., D. W. Roberts, and R. L. Diaper. 2000. Selective oxidation of diaryl sulfides to sulfones with potassium hydrogen persulfate. Sulfur Lett. 23(3):139–144.
53. White, P. D. 2000. Fmoc Solid Phase Peptide Synthesis: A Practical Approach. Oxford University Press, Oxford, UK.
54. Xu, Q., E. A. Ottinger, N. A. Sole, and G. Barany. 1997. Detection and minimization of H-phosphonate side reaction during phosphopeptide synthesis by a post-assembly global phosphorylation strategy. Lett. Pept. Sci. 3(6): 333–342.
55. Zalipsky, S. 1995. Chemistry of polyethylene glycol conjugates with biologically active molecules. Adv. Drug Delivery Rev. 16(2,3):157–182.
56. Zalipsky, S. 1995. Functionalized Poly(ethylene glycols) for Preparation of Biologically Relevant Conjugates. Bioconjugate Chem. 6(2):150–165.
57. Zalipsky, S., and J. M. Harris. 1997. Introduction to chemistry and biological applications of poly(ethylene glycol). ACS Symp. Ser.(Poly(ethylene glycol). 680:1–13. Each of the above references is hereby incorporated by reference.

Although the present invention has been described with reference to specific details, it is not intended that such details should be regarded as limitations upon the scope of the invention, except as and to the extent that they are included in the accompanying claims.

What is claimed is:

1. A trifunctional composition of matter comprising: a trifunctional linker moiety including as groups bonded thereto (a) an alkyl chain for attachment to a substrate, (b) a fluorescent moiety for generating a fluorescent signal, and (c) a recognition moiety having a spacer group of a defined length thereon, said recognition moiety having a binding affinity with tetrameric multivalent neuramimidase.

2. The trifunctional composition of matter of claim 1 wherein said recognition moiety includes at least one group selected from a carboxylate group, an N-acetyl group and a guanidinium group thereon.

* * * * *